United States Patent [19]

Kirst

[11] Patent Number: 4,458,065

[45] Date of Patent: Jul. 3, 1984

[54] 7-N-(SUBSTITUTED-APRAMYCIN ANTIBIOTIC DERIVATIVES AND INTERMEDIATES THEREFOR

[75] Inventor: Herbert A. Kirst, Indianapolis, Ind.

[73] Assignee: Eli Lilly and Company, Indianapolis, Ind.

[21] Appl. No.: 467,418

[22] Filed: Feb. 17, 1983

[51] Int. Cl.³ .............................................. C07H 15/22
[52] U.S. Cl. .................................... 536/16.8; 536/8.1
[58] Field of Search ............................... 536/16.8, 18.1

[56] References Cited

U.S. PATENT DOCUMENTS

| | | | |
|---|---|---|---|
| 4,223,024 | 9/1980 | McAlpine et al. | 536/16.8 |
| 4,239,752 | 12/1980 | Carney et al. | 536/16.8 |
| 4,358,585 | 11/1982 | Igarashi et al. | 536/16.8 |
| 4,360,665 | 11/1982 | Kirst | 536/16.8 |
| 4,370,475 | 1/1983 | Igarashi et al. | 536/16.8 |
| 4,379,917 | 4/1983 | Kirst | 536/16.8 |

OTHER PUBLICATIONS

H. A. Kirst et al., *Tet. Letters*, vol. 22, p. 295, (1981, approximately the first quarter of the year).
J. Davies et al., *Antimicrob. Agents Chemother.*, 14, 69 (1978).
S. O'Connor et al., *J. Org. Chem.*, 41, 2087 (1976).
Y. Abe et al., *J. Antibiotics*, (Tokyo), 34, 1434 (1981).
Kirst et al., Serial Nos. 304,292 and 304,291, filed 9/21/81, and Serial Nos. 415,122 and 415,207, filed 9/7/82.

*Primary Examiner*—Johnnie R. Brown
*Attorney, Agent, or Firm*—Paul C. Steinhardt; Arthur R. Whale

[57] ABSTRACT

Apramycin derivatives substituted at the 7'-amino group with a methyl, ethyl, n-propyl or n-butyl substituent are broad spectrum antibiotics. Also claimed are intermediates in the synthesis of these 7'-N-alkylapramycin derivatives.

13 Claims, No Drawings

7-N-(SUBSTITUTED-APRAMYCIN ANTIBIOTIC DERIVATIVES AND INTERMEDIATES THEREFOR

BACKGROUND OF THE INVENTION

This invention relates to antibiotic derivatives of apramycin and intermediates in the synthesis therefor. In particular, it relates to apramycin derivatives in which the 7'-amino group is derivatized by a $C_1$ to $C_4$-alkyl group; and the pharmaceutically acceptable acid addition salts thereof.

Apramycin is used as a veterinary antibiotic (see U.S. Pat. Nos. 3,691,279, 3,853,709 and 3,876,767) and has the following structure:

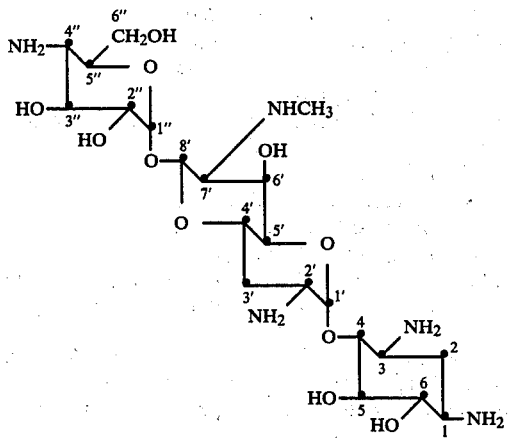

It is known in the art that substitution on various positions of the aminoglycoside rings may increase the activity relative to the parent aminoglycoside, especially against bacteria resistant to the parent aminoglycoside. Some recent substituted-apramycin derivatives, in which the 1, 3 and 2'-amino groups were derivatized, have been recently reported by Herbert A. Kirst, Brenda A. Truedell and John E. Toth in *Tetrahedron Letters*, vol. 22, pp 295-298 (1981).

The apramycin derivatives of the instant application are modified on the 7'-amino group and possess broad-spectrum antibiotic activity while differing in structure from the aforementioned compounds and other compounds previously disclosed in the art.

SUMMARY OF THE INVENTION

The 7'-N-alkylapramycin antibiotics of this invention are represented by the following formula:

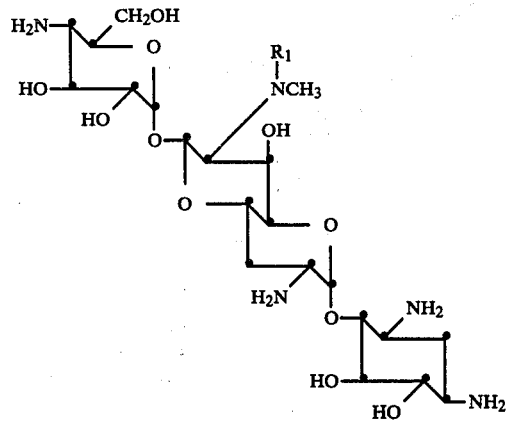

wherein $R_1$ is methyl, ethyl, n-propyl or n-butyl; and the pharmaceutically acceptable acid addition salts thereof.

A second aspect of this invention provides intermediates useful in the synthesis of the above apramycin antibiotics, represented by the following formula:

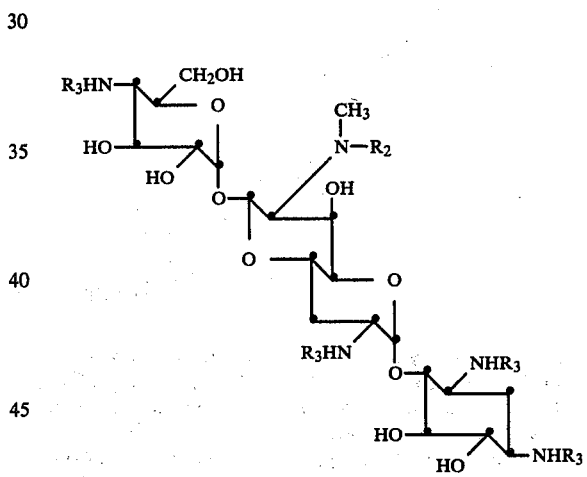

wherein $R_2$ is hydrogen, methyl, ethyl, n-propyl or n-butyl and $R_3$ is acetyl, $C_1$ to $C_4$-alkoxycarbonyl, $C_1$ to $C_4$-(substituted)alkoxycarbonyl, phenoxycarbonyl, benzyloxycarbonyl or substituted benzyloxycarbonyl.

DETAILED DESCRIPTION OF THE INVENTION

This invention is directed to certain 7'-N-alkylapramycin antibiotic compounds and the intermediates in the synthesis of these antibiotics.

In one aspect, the instant invention provides 7'-N-alkylapramycin antibiotic compounds of formula 1

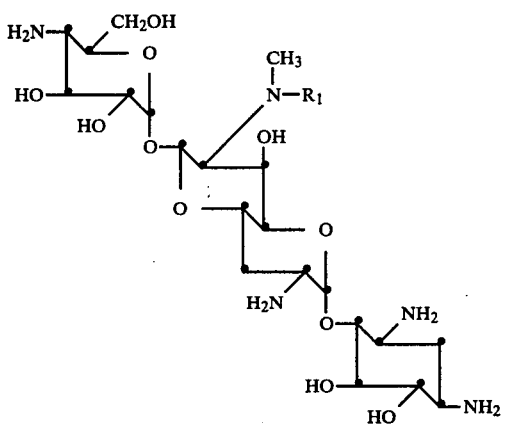

wherein $R_1$ is methyl, ethyl, n-propyl or n-butyl; and the pharmaceutically acceptable acid addition salts thereof.

A second aspect of the instant invention encompasses 1,3,2',4"-tetra-N-protected apramycin intermediate compounds of the formula 2

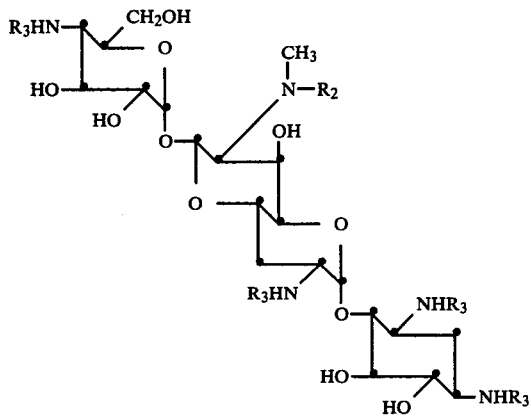

wherein $R_2$ is hydrogen, methyl, ethyl, n-propyl or n-butyl and $R_3$ is acetyl, $C_1$ to $C_4$-alkoxycarbonyl, $C_1$ to $C_4$-(substituted)alkoxycarbonyl, phenoxycarbonyl, benzyloxycarbonyl, or substituted benzyloxycarbonyl.

As used in the instant application, the term "pharmaceutically acceptable acid addition salts" means those formed by standard acid-base reactions between the appropriate aminoglycoside and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, salicylic, methanesulfonic, benzenesulfonic, sorbic, picric, benzoic, cinnamic, and like acids.

As used in the instant application, the term "$C_1$ to $C_4$-alkoxycarbonyl" means methoxycarbonyl, ethoxycarbonyl, n-propoxycarbonyl or n-butoxycarbonyl. Similarly, the term $C_1$ to $C_4$-(substituted)alkoxycarbonyl means amino protecting groups of this class known to those skilled in the art, e.g. 2,2,2-trichloroethoxycarbonyl, 2-iodoethoxycarbonyl, 2-trimethylsilylethoxycarbonyl, 2-(p-toluenesulfonyl)ethoxycarbonyl or other such groups that can be removed by reductive or basic hydrolytic means.

The term "substituted benzyloxycarbonyl" denotes amino protecting groups such as 2,4,6-trimethylbenzyloxycarbonyl, p-methoxybenzyloxycarbonyl, p-nitrobenzyloxycarbonyl, m-chlorobenzyloxycarbonyl, 2,4-dichlorobenzyloxycarbonyl, and like groups that can be removed by hydrogenolytic or basic hydrolytic means.

In the foregoing definitions, $C_1$ to $C_4$-(substituted)alkyloxycarbonyl and substituted benzyloxycarbonyl groups are not exhaustively defined. The function of such groups is merely to protect the primary amino groups from alkylation while the C-7'-amino group is being alkylated, then to be removed without disrupting the rest of the apramycin skeleton. Other substituted benzyloxycarbonyl and $C_1$ to $C_4$-(substituted)alkoxycarbonyl amino-protecting groups are known in the art, and meet the above criteria so as to be suitable in the synthesis of the intermediate and antibiotic compounds of this invention.

Exemplary 7'-N-alkylapramycin antibiotic compounds of the instant invention include:
7'-N-methylapramycin,
7'-N-ethylapramycin,
7'-N-(n-propyl)apramycin,
7'-N-(n-butyl)apramycin,
7'-N-ethylapramycin hydrochloride,
7'-N-(n-propyl)apramycin sulfate,
7'-N-(n-butyl)apramycin phosphate,
7'-N-ethylapramycin acetate and
7'-N-(n-propyl)apramycin succinate.

Preferred 7'-N-alkylapramycin antibiotic compounds of the instant invention include:
7'-N-ethylapramycin,
7'-N-ethylapramycin hydrochloride,
7'-N-ethylapramycin sulfate, and
7'-N-ethylapramycin phosphate.

The more preferred 7'-N-alkylapramycin antibiotic compound of the instant invention is 7'-N-ethylapramycin.

Examples of the 7'-N-alkyl-1,3,2',4"-tetra-N-protected apramycin intermediate compounds (i.e., wherein $R_2$ is methyl, ethyl, n-propyl or n-butyl) of the instant invention include:
7'-N-methyl-1,3,2',4"-tetra-N-benzyloxycarbonylapramycin,
7'-N-ethyl-1,3,2',4"-tetra-N-methoxycarbonylapramycin,
7'-N-(n-propyl)-1,3,2',4"-tetra-N-(n-propoxycarbonyl)apramycin,
7'-N-(n-butyl)-1,3,2',4"-tetra-N-(2,2,2-trichloroethoxycarbonyl)apramycin,
7'-N-ethyl-1,3,2',4"-tetra-N-(n-butoxycarbonyl)apramycin,
7'N-(n-propyl)-1,3,2',4"-tetra-N-(phenoxycarbonyl)apramycin,
7'-N-(n-butyl)-1,3,2',4"-tetra-N-(p-methoxybenzyloxycarbonyl)apramycin,
7'-N-ethyl-1,3,2',4"-tetra-N-(n-propoxycarbonyl)apramycin,
7'-N-(n-propyl)-1,3,2',4"-tetra-N-(2,4,6-trimethylbenzyloxycarbonyl)apramycin,
7'-N-(n-butyl)-1,3,2',4"-tetra-N-(n-butoxycarbonyl)apramycin, and
7'-N-methyl-1,3,2',4"-tetra-N-(p-nitrobenzyloxycarbonyl)apramycin.

Preferred examples of the 7'-N-alkyl-1,3,2',4"-tetra-N-protected apramycin intermediate compounds include:
7'-N-methyl-1,3,2',4"-tetra-N-acetylapramycin,
7'-N-ethyl-1,3,2',4"-tetra-N-acetylapramycin, 7'-N-(n-propyl)-1,3,2',4''-tetra-N-ethoxycarbonylapramycin, 7'-N-(n-butyl)-1,3,2',4''-tetra-N-benzyloxycarbonylapramycin, 7'-N-(n-butyl)-1,3,2',4''-tetra-N-acetylapramycin, 7'-N-(n-propyl)-1,3,2',4''-tetra-N-benzyloxycarbonylapramycin, 7'-N-ethyl-1,3,2',4''-tetra-N-ethoxycarbonylapramycin, 7'-N-ethyl-1,3,2',4''-tetra-N-benzyloxycarbonylapramycin, 7'-N-methyl-1,3,2',4''-tetra-N-ethoxycarbonylapramycin, and 7'-N-methyl-1,3,2',4''-tetra-N-benzyloxycarbonylapramycin.

The more preferred 7'-N-alkyl-1,3,2',4''-tetra-N-protected apramycin intermediate compounds of this invention are:

7'-N-ethyl-1,3,2',4''-tetra-N-ethoxycarbonylapramycin,

7'-N-ethyl-1,3,2',4''-tetra-N-benzyloxycarbonylapramycin, and

7'-N-ethyl-1,3,2',4''-tetra-N-acetylapramycin,

Examples of the 1,3,2',4''-tetra-N-protected apramycin intermediate compounds (i.e., wherein $R_2$ is hydrogen) of the instant invention include:

1,3,2',4''-tetra-N-methoxycarbonylapramycin, 1,3,2',4''-tetra-N-(n-propoxycarbonyl)apramycin, 1,3,2',4''-tetra-N-(2,2,2-trichloroethoxycarbonyl)apramycin, 1,3,2',4''-tetra-N-(n-butoxycarbonyl)apramycin, 1,3,2',4''-tetra-N-(phenoxycarbonyl)apramycin and 1,3,2',4''-tetra-N-(p-methoxybenzyloxycarbonyl)apramycin.

Preferred 1,3,2',4''-tetra-N-protected apramycin intermediate compounds of the instant invention include:

1,3,2',4''-tetra-N-ethoxycarbonylapramycin, 1,3,2',4''-tetra-N-benzyloxycarbonylapramycin, and 1,3,2',4''-tetra-N-acetylapramycin.

The more preferred 1,3,2',4''-tetra-N-protected apramycin intermediate compounds of the instant invention are:

1,3,2',4''-tetra-N-benzyloxycarbonylapramycin, and 1,3,2',4''-tetra-N-acetylapramycin.

The various compounds and intermediates of the instant invention are made in the general scheme wherein apramycin is first selectively converted to the 1,3,2',4''-tetra-N-protected apramycin intermediate compounds (represented by formula 2, wherein $R_2$ is hydrogen). These intermediate compounds are then alkylated to yield the 7'-N-alkyl-1,3,2',4''-tetra-N-protected apramycin intermediates (represented by formula 2, wherein $R_2$ is methyl, ethyl, n-propyl, n-butyl) which in turn, are converted to the 7'-N-alkylapramycin antibiotic compounds of formula 1 by removal of the N-protecting groups.

More specifically, the 1,3,2',4''-tetra-N-protected apramycin compounds are made by first making an apramycin-carbon dioxide complex. The complex is conveniently made by dissolving apramycin in aqueous sodium bicarbonate and then adjusting the pH of the resultant solution to 7.0 with an acid such as aqueous hydrochloric acid. Lyophilization of this solution then yields a solid apramycin-carbon dioxide complex.

An example of such a procedure for making the apramycin-carbon dioxide complex is to dissolve apramycin (20 mmol) in a solution of sodium bicarbonate (10 mmol) in water (400 ml) and to adjust the pH of the resultant solution from its initial value of 9.0 to 7.0 with 1N hydrochloric acid (approximately 75 ml). After stirring this solution for one hour at room temperature, it can be lyophilized to yield a solid apramycin-carbon dioxide complex.

The 1,3,2',4''-tetra-N-acetylapramycin intermediate compound is made, in general, by dissolving the apramycin-carbon dioxide complex in aqueous methanol and treating the resultant solution with acetic anhydride at room temperature. The tetra-N-acetyl product is then isolated from standard methods such as chromatography with ion-exchange resins or silica gel.

The tetra-N-protected apramycin intermediate can also have $C_1$ to $C_4$-alkoxycarbonyl, $C_1$ to $C_4$-(substituted)alkoxycarbonyl, phenoxycarbonyl, benzyloxycarbonyl or substituted benzyloxycarbonyl as the amino protecting group. These tetra-N-protected apramycin derivatives can be synthesized in a manner analogous to the above tetra-N-acetylapramycin by reacting the apramycin-carbon dioxide complex with the appropriate number or slight excess of molar equivalents of an acylating agent, represented by the following general formula

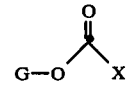

wherein G is $C_1$ to $C_4$-alkyl, $C_1$ to $C_4$-substituted alkyl, phenyl, benzyl or substituted benzyl and X is para-nitrophenoxy, n-oxysuccinimide, N-oxyphthalimide, or a similar activated ester.

For example, the 1,3,2',4''-tetra-N-benzyloxycarbonylapramycin intermediate compound can be made by dissolving the apramycin-carbon dioxide complex (1.0 g) in water (10 ml), diluting with methanol (10 ml) and treating this solution with N-(benzyloxycarbonyloxy)succinimide (1.5 g, 6 mmol) for 24 hours at room temperature.

The 7'-N-alkyl-1,3,2',4''-tetra-N-protected apramycin intermediate compounds are made by alkylating the corresponding 1,3,2',4''-tetra-N-protected apramycin intermediate compounds described above. Active alkylating agents used for this conversion include the alkyl bromides, the alkyl iodides, the alkyl para-toluenesulfonates, and the alkyl methanesulfonates. The alkylating agents are used in an excess of about 5:1 to about 20:1 of the 1,3,2',4''-tetra-N-protected apramycin substrate, with a molar excess of about 10:1 being preferred. The temperatures of this reaction may range from room temperature to about 80° C., with room temperature or moderate heating being preferred. The solvent used for the reaction should be a polar aprotic organic solvent such as dimethylformamide, dimethylsulfoxide, hexamethylphosphoramide, acetonitrile or acetone, or mixtures thereof.

The general procedure for the synthesis of the 7'-N-alkylapramycin antibiotic compounds of the instant invention entails deprotecting the 1,3,2', and 4'' amino groups of the above 7'-N-alkyl-1,3,2',4''-N-protected apramycin intermediate compounds. The deprotection procedures necessary to effect this conversion are well known to those skilled in the aminoglycoside antibiotic art. For example, the acetyl amino-protecting group can be removed by refluxing the compound to be deprotected in ethanol solution with hydrazine hydrate. The benzyloxycarbonyl amino-protecting group and the substituted benzyloxycarbonyl amino-protecting groups can be removed by dissolving the N-protected intermediate in a solvent such as aqueous ethanol and hydrogenating this solution over a hydrogenation catalyst such as palladium/carbon. The alkoxycarbonyl, substituted alkoxycarbonyl and phenoxycarbonyl groups can be removed by basic hydrolysis using for example, barium hydroxide in warm ethanol.

The isolation and purification of the various intermediates and antibiotic compounds encompassed in the instant invention is accomplished by methods well known in the art of aminoglycoside antibiotics, as exemplified by the procedures described in the following Experimental section.

The 7'-N-alkylapramycin antibiotic compounds of this invention, in either their free base form or their pharmaceutically acceptable acid addition salt form, are useful for treating infections caused by gram-positive and gram-negative bacteria in warm-blooded animals. The compounds can be administered parenterally, in the free base form or in the pharmaceutically acceptable acid addition salt form, using pharmaceutically acceptable formulations known in the art. The compounds can also be administered as veterinary compositions, for example, in the feed or drinking water of farm animals to treat infections such as colibacillosis or swine dysentery.

Alternatively, the compounds can be used as a surface disinfectant. Solutions containing as little as 0.1% by weight of the antibiotic are effective for disinfecting purposes. Such solutions, preferably also containing a detergent or other cleansing agent, are useful for disinfecting objects such as glassware, dental and surgical instruments, and surfaces such as walls, floors, and tables in areas where the maintenance of sterile conditions is important, i.e., hospitals, food-preparation areas, and the like.

The antibacterial activity of the 7'-N-alkylapramycin antibiotic compounds of this invention is similar to apramycin and extends to gram-positive bacteria such as *Staphylococcus aureus, Staphylococcus epidermis, Streptococcus pyogenes*, and *Streptococcus pneumoniae*, and gram-negative bacteria such as *Haemophilus influenzae, Shigella sonnei, Escherichia coli, Klebsiella pneumoniae, Enterobacter aerogenes, Enterobacter cloacae, Salmonella typhi, Pseudomonas aeruginosa, Serratia marcescens, Proteus morganii, Proteus inconstans, Proteus rettgeri,* and *Citrobacter freundii.*

The 1,3,2',4"-tetra-N-protected apramycin intermediate compounds and the 7'-N-alkyl-1,3,2',4"-tetra-N-protected apramycin intermediate compounds of formula 2 are useful in the synthesis of the 7'-N-alkylapramycin antibiotic compounds, represented by formula 1, as discussed above.

The following Examples (1–4) in the Experimental Section are provided to further illustrate this invention. It is not intended that this invention be limited in scope by reason of any of the following Examples.

In the following Experimental Section, carbon-13 nuclear magnetic resonance spectra, field desorption mass spectra and high performance liquid chromatography are abbreviated C-13 n.m.r., f.d.m.s., and HPLC, respectively. The nuclear magnetic resonance spectra were obtained either on a Varian Associates FT80 spectrometer or a Jeol JNM-PS-100 spectrometer, using dioxane as the internal standard. The chemical shifts are expressed in δ values (parts per million downfield from tetramethylsilane). The field desorption mass spectra were taken on a Varian-MAT 731 spectrometer using carbon dendrite emitters. The high performance liquid chromatography was carried out on a Waters Associates, Inc. Prep. 500 Instrument.

Column chromatography was often carried out using an ion exchange resin such as BioRex AG50 W-X4 or BioRex 70 as the stationary phase. Both BioRex AG50 W-X4 and BioRex 70 are acidic cation ion-exchange resins. Both of these resins are obtained from Bio-Rad Labs., 2200 Wright Avenue, Richmond, Ca. 94804. Thin layer chromatography was carried out on E. Merck silica gel plates.

The abbreviations "mmol" and "h" stand for millimole and hour, respectively.

EXAMPLE 1

1,3,2',4"-Tetra-N-Acetylapramycin

Apramycin (10.8 g, 20 mmol) and sodium bicarbonate (8.4 g, 100 mmol) were dissolved in water (400 ml) and the pH of the resultant solution was adjusted from its initial value of 9.1 to 7.0 with 1N hydrochloric acid (75 ml). The solution was stirred for 1 h at room temperature and then was lyophilized. The lyophilized complex was dissolved in water (200 ml) and the solution was diluted with methanol (200 ml) and treated with acetic anhydride (10 ml). After stirring overnight at room temperature, the solution was concentrated to aqueous under reduced pressure and then lyophilized. The crude product was dissolved in water (30 ml), the pH of the solution was adjusted to 7, and the solution was loaded on a column of BioRex AG50 W-X4 (500 ml resin, H+ cycle, pH 4.5). The column was eluted with water (1 liter) and a linear gradient of water (1 liter) and 0.1N ammonium hydroxide (1 liter). Fractions containing the desired product were located by thin layer chromatography analysis, combined and lyophilized to yield 10.3 g (73%) of 1,3,2',4"-tetra-N-acetylapramycin: C-13 n.m.r. ($D_2O$, pH 8.6), δ22.7, 22.9(2X), 23.5, 29.6, 32.7, 33.5, 48.7, 49.3, 50.2, 52.3, 61.6, 62.6, 65.8, 67.4, 71.0, 71.1, 71.8, 72.4, 75.4, 77.5, 81.8, 95.1, 96.3, 174.1, 174.2, 174.8, and 175.4.

EXAMPLE 2

1,3,2',4"-Tetra-N-Benzyloxycarbonylapramycin

Apramycin complex, prepared as described in Example 1, (1.0 g, 1 mmol) was dissolved in water (10 ml) and the solution was diluted with methanol (10 ml). N-(benzyloxycarbonyloxy)succinimide (1.5 g, 6 mmol) was added to the solution and the resultant solution was stirred for 24 h at room temperature. The reaction mixture was evaporated to dryness under reduced pressure. The resultant crude reaction product was slurried with BioRex AG50 W-X4 (25 ml, H+ cycle, washed to pH 5) in a column and then eluted with water (approximately 500 ml) to remove the water-soluble and non-adsorbed material.

The column was then emptied into a saturated aqueous sodium carbonate solution, and this mixture was extracted twice with ethyl acetate. The combined ethyl acetate extracts were dried over sodium sulfate, filtered and evaporated to dryness, to yield 0.98 g of 1,3,2',4"-tetra-N-benzyloxycarbonylapramycin as a white amorphous powder: F.D.M.S.: m/e 1075.

EXAMPLE 3

7'-Ethyl-1,3,2',4''-Tetra-N-acetylapramycin 1,3,2',4''-Tetra-N-acetylapramycin (1.06 g, 1.5 mmol) was dissolved in dimethylformamide (75 ml) and the solution was treated with ethyl iodide (4.68 g) while stirring overnight at room temperature. The solvent was then removed from the reaction solution under reduced pressure to yield 7'-N-ethyl-1,3,2',4''-tetra-N-acetylapramycin.

EXAMPLE 4

7'-N-Ethylapramycin

The 7'-N-ethyl-1,3,2',4''-tetra-N-acetylapramycin from Example 3 above was dissolved in hydrazine hydrate (200 ml) and the solution was refluxed for 40 h. After cooling to room temperature, the solvent was evaporated under reduced pressure. The resultant residue was dissolved in water (15 ml) and the solution was adjusted to pH 10 before loading it on a column of BioRex 70 ($NH_4^+$ cycle, pH 10). The column was eluted with a linear gradient of 0.01N ammonium hydroxide (1 liter) and 0.1N ammonium hydroxide (1 liter). Fractions were analyzed by thin layer chromatography and the appropriate fractions were combined and lyophilized to yield 58 mg. of 7'-N-ethylapramycin along with 48 mg of a mixture of apramycin and 7'-N-ethylapramycin. 7'-N-Ethylapramycin: C-13 n.m.r. ($D_2O$, pH 9.7): δ13.0, 32.8, 36.4, 38.7, 48.8, 49.9, 50.3, 51.3, 53.1, 61.4, 64.2, 68.0, 68.7, 71.1, 71.9, 73.7, 74.9, 76.8, 78.2, 87.6, 96.3(2X) and 101.4. F.D.M.S.: m/e 586 (P+1).

I claim:

1. A compound of the formula

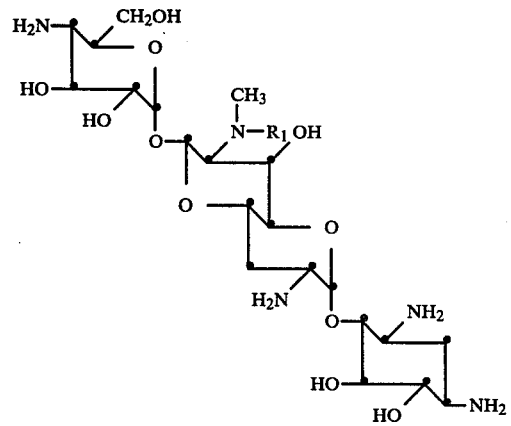

wherein $R_1$ is methyl, ethyl, n-propyl or n-butyl; and the pharmaceutically acceptable acid addition salts thereof.

2. A compound of claim 1, wherein $R_1$ is ethyl.
3. The compound of claim 2, wherein the compound is the free base.
4. A compound of the formula

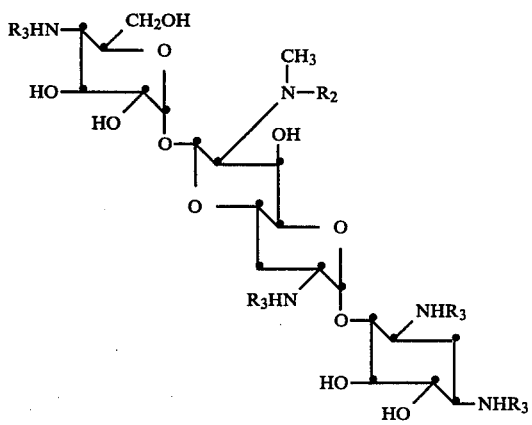

wherein $R_2$ is hydrogen, methyl, ethyl, n-propyl or n-butyl and $R_3$ is acetyl, $C_1$ to $C_4$-alkoxycarbonyl, $C_1$ to $C_4$-(substituted)alkoxycarbonyl, phenoxycarbonyl, benzyloxycarbonyl or substituted benzyloxycarbonyl.

5. A compound of claim 4, wherein $R_2$ is methyl, ethyl, n-propyl or n-butyl.
6. A compound of claim 5, wherein $R_3$ is $C_1$ to $C_4$-alkyloxycarbonyl, benzyloxycarbonyl, substituted benzyloxycarbonyl or acetyl.
7. A compound of claim 6, wherein $R_3$ is ethoxycarbonyl, benzyloxycarbonyl or acetyl.
8. A compound of claim 7, wherein $R_2$ is ethyl.
9. A compound of claim 4, wherein $R_2$ is hydrogen.
10. A compound of claim 9, wherein $R_3$ is $C_1$ to $C_4$-alkoxycarbonyl, benzyloxycarbonyl, substituted benzyloxycarbonyl or acetyl.
11. A compound of claim 10, wherein $R_3$ is benzyloxycarbonyl or substituted benzyloxycarbonyl.
12. A compound of claim 11, wherein $R_3$ is benzyloxycarbonyl.
13. A compound of claim 10, wherein $R_3$ is acetyl.